United States Patent [19]
Robertson

[11] Patent Number: 4,999,304
[45] Date of Patent: Mar. 12, 1991

[54] DYNAMIC BRAKING CENTRIFUGE

[75] Inventor: Steven Robertson, Elkhart, Ind.
[73] Assignee: Miles Inc., Elkhart, Ind.
[21] Appl. No.: 138,096
[22] Filed: Dec. 28, 1987
[51] Int. Cl.⁵ ............................ G01N 1/10; G01N 9/30
[52] U.S. Cl. ........................................ 436/45; 422/72; 422/237; 435/2; 436/177; 436/179
[58] Field of Search .................... 436/45, 177, 179; 422/72, 237

[56] References Cited

U.S. PATENT DOCUMENTS

| | | | |
|---|---|---|---|
| 3,151,073 | 10/1960 | Anthon | 422/72 |
| 3,795,451 | 3/1974 | Mailen | 422/72 |
| 3,829,223 | 8/1974 | Hamel | 422/72 |
| 3,899,296 | 8/1975 | Mailen et al. | 422/72 |
| 4,284,602 | 8/1981 | Kelton et al. | 422/72 |
| 4,740,472 | 4/1988 | Burtis et al. | 436/45 |
| 4,814,282 | 3/1989 | Holen et al. | 422/72 |

FOREIGN PATENT DOCUMENTS

| | | | |
|---|---|---|---|
| 1190839 | 7/1985 | Canada | 422/72 |
| 0073512 | 3/1983 | European Pat. Off. | 422/72 |
| 89/00458 | 1/1989 | PCT Int'l Appl. | |

*Primary Examiner*—Robert A. Wax
*Assistant Examiner*—Janelle D. Waack
*Attorney, Agent, or Firm*—Roger N. Coe

[57] ABSTRACT

A centrifuge for separating constituents of fluids, diluting the constituents and inoculating a reagent includes a spinning assembly for spinning a processor member. The processor member includes fluid and diluent compartments, separation chambers for a fluid and for a diluent, a mixing chamber, and a reagent chamber. The fluid compartment is in communication with the fluid separation chamber by a first passage. The diluent compartment and diluent separation chamber are communicated by a second passage. The first and second passages are oriented such that centrifugal force moves the fluid and diluent through the first and second passages into the respective chambers. The chambers are aligned to prevent outflow under the influence of centrifugal force but to allow outflow into measuring passages upon braking the spinning of the processor member. Spinning the processor member after braking generates a centrifugal force moving the fluid and diluent through the measuring passages into a mixing chamber. Braking the spinning of the processor member again applies a braking force on the mixed fluid and diluent moving this mixture into the reagent chamber.

1 Claim, 1 Drawing Sheet 4,999,304

DYNAMIC BRAKING CENTRIFUGE

BACKGROUND OF THE INVENTION

A. Field of the Invention

The present invention relates to devices for separating constituents from fluids, performing a dilution, and inoculating a reagent; and, more particularly, the present invention relates to a centrifuge capable of spinning and stopping rapidly with the aid of dynamic braking and a processing member mountable on the centrifuge for performing the separating, diluting and inoculating functions; and to a new and improved method of separating constituents from a fluid, performing a dilution, and inoculating a reagent.

B. Description of the Background Art

Chemical tests for analyzing fluids such as whole blood often apply centrifugal force to fluid contained in a processor card to separate constituents, such as plasma, from the fluid, mix the constituents with a diluent and combine the diluted sample with reagent. Each of the functions (separating, diluting and combining with reagent) must be performed sequentially, and this requires moving the fluid and diluent to a location, performing a function, and moving the fluid to a different location to perform the next function. Examples of devices for performing these tests are provided in U.S. Pat. Nos. 4,690,899; 3,899,296; 4,456,581; 4,557,600; and 4,515,889.

One procedure to move fluid through a processor card to perform the different functions is to change the position of the processor card on a centrifuge relative to the central axis of rotation. By changing the position of a processor card, different portions of the processor card are aligned with the radial centrifugal force vectors, thus moving the fluid in different directions.

Another procedure for separating, diluting and mixing a fluid and inoculating a reagent pad is described in European Patent Application No. 85 105 106.0, filed Apr. 26, 1985. This procedure employs a centrifuge with an assembly for rotating a processor card on the centrifuge. Rotating the processor card aligns different portions of the processor card with the centrifugal force vector. By rotating the position of a processor card on a centrifuge the centrifugal force acts on the fluid and diluent in the processor card to move the fluid and diluent in different directions within the processor card. Centrifugal force acting in a first direction, for example, will move the fluid and diluent to a first position. While the fluid and diluent are in the first position, a testing procedure can be performed. Once the testing procedure is completed, the direction of centrifugal force can be changed by turning the processor card. The centrifugal force will move the fluid and diluent to a second position for a second test.

The devices that move a processor card or change the direction of centrifugal force are expensive since they require complex movable structures More frequent servicing of these devices is also required due to the more complex structures. It is desirable to provide a system capable of moving fluids and diluents between different testing locations within a processor card without the necessity of additional structure being added to the centrifuge for maneuvering the card.

SUMMARY OF THE INVENTION

An object of the present invention is to provide a new and improved device for separating constituents of a fluid, performing a dilution, and inoculating a reagent.

Another object of the present invention is to provide a new and improved method for separating constituents of a fluid, performing a dilution, and inoculating a reagent.

A further object of the present invention is to provide a new and improved device for separating plasma from whole blood, performing a dilution using centrifugal force, and inoculating a reagent pad using dynamic braking.

A still further object of the present invention is to provide a new and improved method for separating plasma from whole blood, performing a dilution using centrifugal force, and inoculating a reagent pad using dynamic braking.

Briefly, the present invention is directed to a new and improved centrifuge and processor card which use centrifugal force and dynamic braking to separate constituents of a fluid, perform a dilution and inoculate a reagent pad area, and to a new and improved method for performing these steps. In accordance with the principles of the present invention, a centrifuge is provided for rotating a rotating member or processor card about an axis of rotation. The processor card or rotating member includes separate compartments for the fluid to be tested, a diluent and a reagent. The compartments communicate through passages with separate separation chambers. These passages are aligned relative to the axis of rotation such that the centrifugal force acts on the fluid and diluent to move them through the passages. The separation chambers are oriented to collect the fluid and diluent and prevent further movement through the processor card under the influence of centrifugal force.

Each separation chamber includes an outlet in communication with measuring capillaries. To move the fluid and diluent to the next stage of testing, the rotation of the processor card is stopped suddenly. The resulting braking force moves the fluid and diluent into the measuring capillaries. The processor card is again spun, and the centrifugal force moves the fluid and diluent in the measuring capillaries into a mixing chamber. During continued spinning of the processor card, the fluid and diluent remain in the mixing chamber and are mixed by varying the rotational speed. After the fluid and diluent are completely mixed, the rotation is again stopped suddenly and the braking force moves the diluted fluid out of the mixing chamber and onto a reagent pad.

BRIEF DESCRIPTION OF THE DRAWING

Other and further objects, advantages and features of the present invention will be apparent to those skilled in the art from the following detailed description taken in conjunction with the accompanying drawing in which.

DESCRIPTION OF THE PREFERRED EMBODIMENTS

Figure 1:
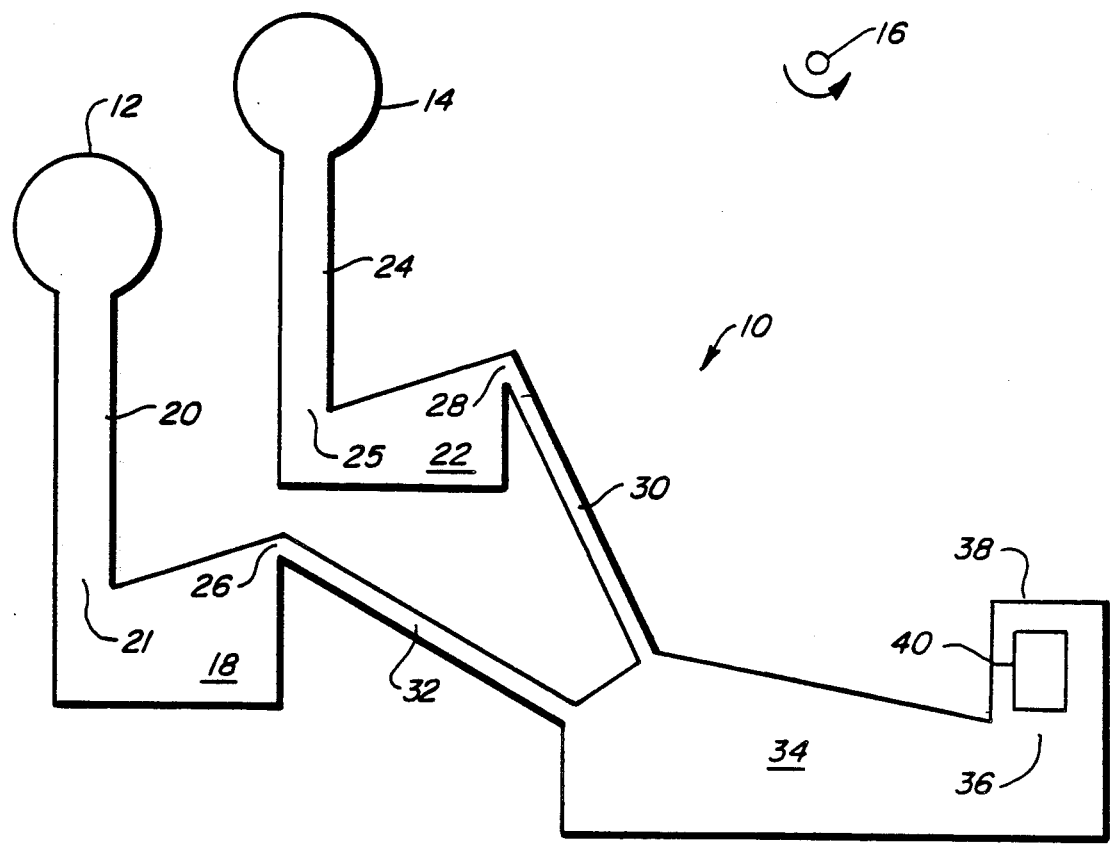
FIG. 1 is a schematic illustration of processor card constructed in accordance with the principles of the present invention.

Analytical chemical testing techniques, including testing to determine blood chemistries, immunological testing for analyzing fluids, particularly body fluids, as well as a number of other liquid analytical chemical techniques, typically apply centrifugal force on a processor card such as the rotating member or processor card generally designated by the reference numeral 10. The processor card 10 can be used in most tests and for testing many different fluids. For the purposes of the present description, the processor card 10 will be described for the testing of whole blood.

Prior to testing, a sample of whole blood is introduced into a whole blood compartment 12, and a diluent is introduced into a diluent compartment 14. To commence the testing procedure, the processor card 10 is mounted on a centrifuge (not shown) and rotated counterclockwise about an axis of rotation 16.

The whole blood compartment 12 communicates with a whole blood separation chamber 18 through a passage 20 and an inlet 21 in the whole blood separation chamber 18. Similarly, the diluent compartment 14 communicates with a diluent holding chamber 22 through a passage 24 and an inlet 25 in the diluent holding chamber 22. The whole blood compartment 12, the passage 20, the whole blood separation chamber 18, the diluent compartment 14, the passage 24 and the diluent holding chamber 22 are each aligned relative to the axis of rotation 16 such that centrifugal force moves the whole blood and diluent through the passages 20 and 24, respectively, and into the whole blood separation chamber 18 and the diluent holding chamber 22, respectively.

The whole blood separation chamber 18 and an outlet 26 in the whole blood separation chamber 18 are oriented relative to the axis of rotation 16 and the inlet 21 to prevent flow of whole blood out of whole blood separation chamber 18 under the influence of centrifugal force. The diluent holding chamber 22 and an outlet 28 in the diluent holding chamber 22 are also oriented relative to the axis of rotation 16 and the inlet 25 to prevent the flow of diluent out of the diluent holding chamber 22 under the influence of centrifugal force.

While the whole blood is in the blood separation chamber 18, the processor card 10 is centrifuged by rotating about axis 16 to allow separation of the solid and liquid constituents of the whole blood. Once separation is completed, the rotation of the processor card 10 is stopped quickly. The braking force developed by the quick deceleration forces the diluent to move toward the axis of rotation 16 and through the outlet 28 into a measuring capillary 30. Simultaneously, the separated liquid constituent is forced through outlet 26 into a measuring capillary 32. Since most fluid chemistry tests require precisely measured samples, the measuring capillaries 30 and 32 are adapted to receive a measured quantities of fluid.

Once diluent has been moved into measuring capillary 30 and liquid constituent into measuring capillary 32, the centrifuge is energized to rotate or spin the processor card 10. The resultant centrifugal force moves the measured diluent and liquid constituent out of the capillaries 30 and 32, respectively, and into a mixing chamber 34. The mixing chamber 34 includes an outlet 36 oriented relative to the axis of rotation 16 to prevent exit of the diluent or liquid constituent through outlet 36 under the influence of centrifugal force. Once diluent and liquid constituent are in the mixing chamber 34, the speed of rotation can be varied to swirl the fluids in the mixing chamber 34, thereby thoroughly mixing the diluent and liquid constituent.

Once the diluent and liquid constituent have been mixed, the centrifuge is stopped quickly. The resulting braking force forces the mixed fluid through the outlet 36, into a reagent chamber 38 and onto a reagent pad 40. Chemical testing can be performed by measuring the reaction in the reagent pad 40.

Since the motion of the fluid and liquid constituent is toward the axis of rotation 16 when braking force is applied and away from the axis of rotation 16 when centrifugal force is applied, one arrangement of the compartments, passages and chambers in the processor card 10 is that each successive station is farther from the axis of rotation 16 than the prior station. In addition, the inlet to each station is farther from the axis of rotation than the outlet.

The processor card 10, by using centrifugal force and braking force, is able to perform chemical testing. The processor card 10 differs from the prior art, however, in that the need for additional mechanical structure on the centrifuge to vary the direction of centrifugal force acting on the card 10 is not required. Moreover, the spinning and braking sequence of the centrifuge and processor card 10 can be performed manually or the sequence can be automated.

The resulting dynamic braking centrifugal of the present invention provides more reliable transfer of fluids and mixing of fluids than prior art devices which have relied upon capillary action alone for such functions.

Many modifications and variations of the present invention are possible in light of the above teachings Thus, it is to be understood that, within the scope of the appended claims, the invention can be practiced other than as specifically described in the above description. It will be understood that the size and shape of the compartments, passageways and chambers can be varied. In addition, other compartments, passageways and chambers can be added to the system for more complicated dilutions and reaction procedures.

What is claimed is:

1. An assembly for separately and simultaneously delivering and then mixing multiple fluids, comprising:
    a rotating member having an axis of rotation;
    means for rotating said rotating member about said axis of rotation and periodically varying the speed of said rotating member;
    said rotating member including a first compartment for containment of a first fluid and a separation chamber which is in communication with said first compartment by means of a first passage, wherein said first passage is in preselected alignment relative to said axis of rotation to allow movement of said first fluid along said first passage from said first compartment to said separation chamber under the influence of centrifugal force;
    said rotating member also including a first measuring passage in communication with said separation chamber, said first measuring passage aligned relative to said axis of rotation to prevent the flow of said first fluid into the first measuring passage under the influence of centrifugal force but capable of allowing the flow a selected portion of a third fluid obtained from said first fluid in said separation chamber into said first measuring passage upon the influence of a breaking force applied to said rotating member;
    said rotating member additionally including a second compartment for containment of a second fluid and a holding chamber which is in communication with said second compartment by means of a second passage, wherein said second passage is in preselected alignment relative to said axis of rotation to allow movement of said second fluid along said second passage from said second compartment to said holding chamber under the influence of centrifugal force;

said rotating member also including a second measuring passage in communication with said holding chamber, said second measuring passage aligned relative to said axis of rotation to prevent the flow of said second fluid into the second measuring passage under the influence of centrifugal force but capable of allowing the flow of a selected portion of said second fluid into said second measuring passage under the influence of a breaking force applied to said rotating member;

said rotating member also including a mixing chamber, said mixing chamber having a first inlet in communication with said first measuring passage and a second inlet in communication with said second passage, wherein upon rotation of said rotating member at least a portion of said second and third fluids flow into said mixing chamber from the respective second and first measuring passages; and said rotating member further including a reagent chamber and an inlet in said reagent chamber, said inlet in said reagent chamber being in communication with said mixing chamber, wherein the mixture resulting from the mixing chamber is introduced into said reagent chamber through said reagent chamber inlet.

* * * * *